US012791546B2

(12) United States Patent
Nour et al.

(10) Patent No.: US 12,791,546 B2
(45) Date of Patent: Nov. 10, 2026

(54) POLYMER FILM RESISTANCE FUEL DETECTOR

(71) Applicants: Saudi Arabian Oil Company, Dhahran (SA); King Abdullah University of Science and Technology, Thuwal (SA)

(72) Inventors: Maha Nour, Thuwal (SA); Ayman Amer, Thuwal (SA); Abdullah Hassan Bukhamsin, Thuwal (SA); Esraa Fakeih, Thuwal (SA); Sumana Bhattacharjee, Thuwal (SA); Khaled Nabil Salama, Thuwal (SA)

(73) Assignees: Saudi Arabian Oil Company, Dhahran (SA); King Abdullah University of Science and Technology, Thuwal (SA)

( * ) Notice: Subject to any disclaimer, the term of this patent is extended or adjusted under 35 U.S.C. 154(b) by 700 days.

(21) Appl. No.: 18/135,539

(22) Filed: Apr. 17, 2023

(65) Prior Publication Data

US 2024/0345060 A1 Oct. 17, 2024

(51) Int. Cl.
*G01N 33/28* (2006.01)
*G01N 31/22* (2006.01)

(52) U.S. Cl.
CPC ........... *G01N 33/28* (2013.01); *G01N 31/223* (2013.01)

(58) Field of Classification Search
CPC ...... G01N 33/28; G01N 31/223; H01C 7/006; H01C 1/012; H01C 17/075; H01C 1/08; H01C 1/14; H01C 3/08; H01C 3/12; H01C 1/084; H10D 89/105; H10D 1/47; H01L 23/5228
See application file for complete search history.

(56) References Cited

U.S. PATENT DOCUMENTS

| | | | | |
|---|---|---|---|---|
| 4,434,233 | A | 2/1984 | Bzdula et al. | |
| 4,829,839 | A | 5/1989 | Fisher et al. | |
| 5,665,844 | A | 9/1997 | Prass et al. | |
| 8,643,388 | B2 | 2/2014 | Hedges et al. | |
| 2003/0003589 | A1* | 1/2003 | Khalil .................. | G01N 21/783 436/167 |
| 2005/0042758 | A1* | 2/2005 | Zyhowski .............. | G01N 31/22 436/3 |

(Continued)

FOREIGN PATENT DOCUMENTS

| | | | |
|---|---|---|---|
| BR | PI1103900 | A2 | 12/2015 |
| CN | 103245634 | A * | 8/2013 |

(Continued)

OTHER PUBLICATIONS

Tan et al., Translated CN 103245634 A "Monolithic Integrated Micro Infrared Gas Sensor", Published Aug. 14, 2013 (Year: 2013).*

(Continued)

*Primary Examiner* — Jennifer Wecker
*Assistant Examiner* — Tracy Ching-Tian Colena
(74) *Attorney, Agent, or Firm* — Fish & Richardson P.C.

(57) ABSTRACT

A system and methods for detecting aromatic compounds mixed with aliphatic compounds are provided. An exemplary system includes a lower substrate, a polymer film including a resistor mesh disposed on the polymer film, and an upper substrate disposed over the polymer film, wherein the upper substrate includes an opening exposing the resistor mesh.

11 Claims, 6 Drawing Sheets

(56) References Cited

U.S. PATENT DOCUMENTS

| | | | | |
|---|---|---|---|---|
| 2008/0095988 | A1* | 4/2008 | Frey | C23F 1/14 427/407.1 |
| 2008/0129193 | A1* | 6/2008 | Asabe | H10K 50/81 257/E51.019 |
| 2013/0152674 | A1 | 6/2013 | Noordover | |
| 2015/0241374 | A1* | 8/2015 | Belbruno | G01N 33/0047 436/501 |
| 2017/0254791 | A1 | 9/2017 | Nink et al. | |
| 2017/0328879 | A1 | 11/2017 | Ayala | |
| 2018/0164263 | A1* | 6/2018 | Fischer | G01N 21/6428 |
| 2019/0019736 | A1* | 1/2019 | Schrauben | H05K 3/046 |
| 2021/0389264 | A1 | 12/2021 | Ito et al. | |
| 2022/0155328 | A1 | 5/2022 | Sliz et al. | |
| 2023/0102451 | A1* | 3/2023 | Matsumoto | C09J 7/10 156/332 |
| 2024/0328980 | A1 | 10/2024 | Nour et al. | |
| 2024/0329030 | A1 | 10/2024 | Nour et al. | |
| 2024/0345026 | A1 | 10/2024 | Nour et al. | |
| 2024/0345061 | A1 | 10/2024 | Kharashi et al. | |
| 2024/0345063 | A1 | 10/2024 | Kharashi et al. | |
| 2024/0345064 | A1 | 10/2024 | Nour et al. | |

FOREIGN PATENT DOCUMENTS

| | | |
|---|---|---|
| CN | 111504850 A | 8/2020 |
| WO | WO 2017213419 A1 | 12/2017 |

OTHER PUBLICATIONS

Agha et al., "A Review of Cyclic Olefin Copolymer Applications in Microfluidics and Microdevices," Macromolecular Materials and Engineering, 2022, 307(2200053): 1-34, 35 pages.

COC Topas Product Brochure, Section 4.2; Table 2, Mar. 2006, 20 pages.

Ghosh et al., "A mass manufacturable thermoplastic based microfluidic droplet generator on cyclic olefin copolymer," J. Micromechanics Microengineering, Apr. 10, 2019, 29(5):055009, 9 pages.

Jain et al., "Design and Simulation of Microfluidic Passive Mixer With Geometric Variation," Int. J. Res. Eng. Technol., Feb. 2016, 5(2):55-58, 4 pages.

Jena et al., "Cyclic olefin copolymer based microfluidic devices for biochip applications: Ultraviolet surface grafting using 2-methacryloyloxyethyl phosphorylcholine," Biomicrofluidics, Mar. 2012, 6(1):012822-1-012822-12, 12 pages.

Jena et al., "Micro fabrication of cyclic olefin copolymer (COC) based microfluidic devices," Microsystem Technologies, Oct. 18, 2011, 18(2):159-166, 8 pages.

Kimmich et al., "Fault detection for modern Diesel engines using signal- and process model-based methods," Control Eng. Pract., Feb. 2005, 13(2):189-203, 15 pages.

Li et al., "Isoelectric focusing in cyclic olefin copolymer microfluidic channels coated by polyacrylamide using a UV photografting method," Electrophoresis, May 2005, 26(9):1800-1806, 7 pages.

McGann et al., "Lean fuel detection with nanosecond-gated laser-induced breakdown spectroscopy," Combustion and Flame, Feb. 2021, 224:209-218, 10 pages.

McGuire et al., "Detection of the aromatic molecule benzonitrile (c-C6H5CN) in the interstellar medium," Science, Jan. 12, 2018, 359(6372):202-205, 4 pages.

Nunes et al., "Cyclic olefin polymers: emerging materials for lab-on-a-chip Applications," Microfluid Nanofluid, Apr. 2010, 9:145-161, 17 pages.

Taghizadeh-Alisaraei et al., "Fault detection of injectors in diesel engines using vibration time-frequency analysis," Applied Acoustics, Jan. 1, 2019, 143:48-58, 11 pages.

* cited by examiner

POLYMER FILM RESISTANCE FUEL DETECTOR

TECHNICAL FIELD

This disclosure relates to a system and method for detecting hydrocarbon fuels blended in paraffin-based lubricants.

BACKGROUND

Fuel smuggling is a growing problem in international commerce. To avoid detection, smugglers may blend hydrocarbon fuels with lubrication oils and greases that are based on paraffinic compounds. Generally, hydrocarbon fuels contain low molecular weight aromatic compounds that can be used to detect the illicit compounds.

SUMMARY

An embodiment described herein provides a system for detecting aromatic compounds mixed with aliphatic compounds. The system includes a lower substrate, a polymer film including a resistor mesh disposed on the polymer film, and an upper substrate disposed over the polymer film, wherein the upper substrate includes an opening exposing the resistor mesh.

Another embodiment described herein provides a method for detecting aromatic compounds mixed with aliphatic compounds. The method includes placing a sample of a test fluid on a polymer film through an opening in an upper substrate, wherein a resistor mesh is disposed on the polymer film. Data collection is started when the sample contacts the resistor mesh, wherein the data collection measures resistivity over time. The data collection is stopped, and a change in resistivity over time is used to determine a test time. The test time is used to determine if an aromatic compound is present in the test fluid.

DETAILED DESCRIPTION

Embodiments described herein provide a system and method for determining the presence of aromatic compounds in lubricants and greases based on paraffinic (aliphatic) compounds. The detection system, herein termed an aromatic detector, is based on the differential solubility of a polymer between aromatic compounds and aliphatic compounds.

A film is formed from a polymer, and then a resistor mesh is deposited over the polymer film. In some embodiments, the resistor mesh is a metal or semiconductor grid deposited by chemical vapor deposition, for example, using a mask. In other embodiments, the resistor mesh is deposited by inkjet printing of a conductive ink. The polymer film with the resistor mesh is mounted in a test apparatus.

To test for the presence of an aromatic compound in the aliphatic compounds, a resistivity instrument is coupled to contact points on the resistor mesh, for example, at the corners of the polymer film. A sample of the test fluid is placed on the polymer film, and if aromatic compounds are present, the polymer film will start to dissolve. The dissolution of the polymer film will result in degradation of the mesh where the test fluid has been applied. The measurement may be conducted for a preselected period of time, such as 1 minute, 2 minutes, 5 minutes, or longer. In some embodiments, the measurement is conducted until the resistivity levels undergoes an inflection point or levels off, indicating that dissolution has slowed or stopped.

For some polymers, contact with a material that is a poor solvent may result in stress cracking, or slower dissolution, leading to breaking of the polymer film under the resistor mesh. However, the dissolution or disintegration rate will be faster for solvents, such as aromatic compounds. In these embodiments, the measurement of the time to an inflection point after the application of the test fluid can be compared to the time to break the polymer film after the application of a control fluid. For example, a paraffinic fluid or paraffinic oil that does not contain aromatics may be used as the control fluid. Similarly, the slope of the increase in resistivity may be lower for a solvent that causes stress cracking. Accordingly, the slope may be used as an indicator of the presence of aromatic compounds in the aliphatic compounds.

Figure 1A:
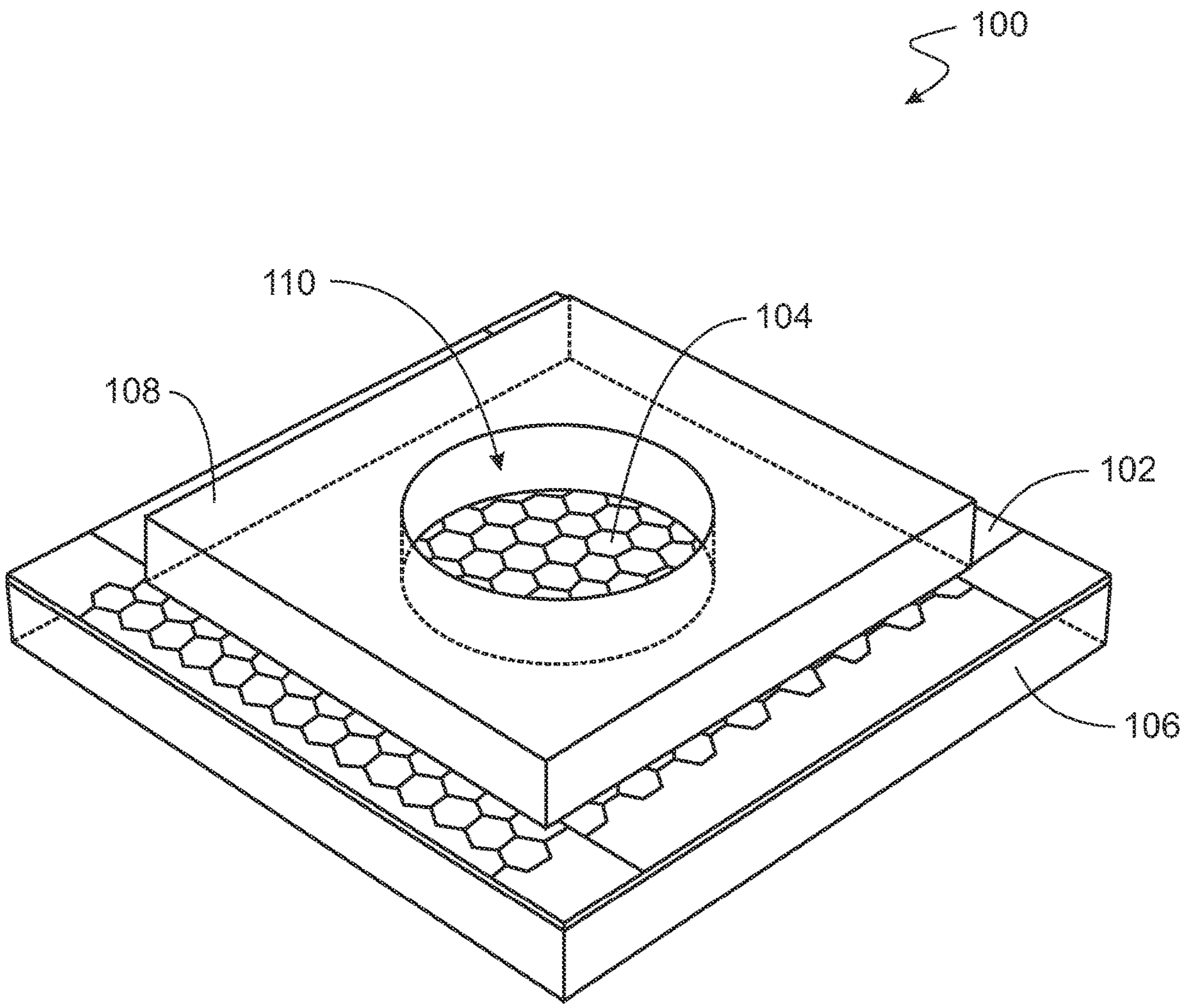
FIG. 1A is a perspective view of an aromatics detector based on a polymer film.
Figure 1B:
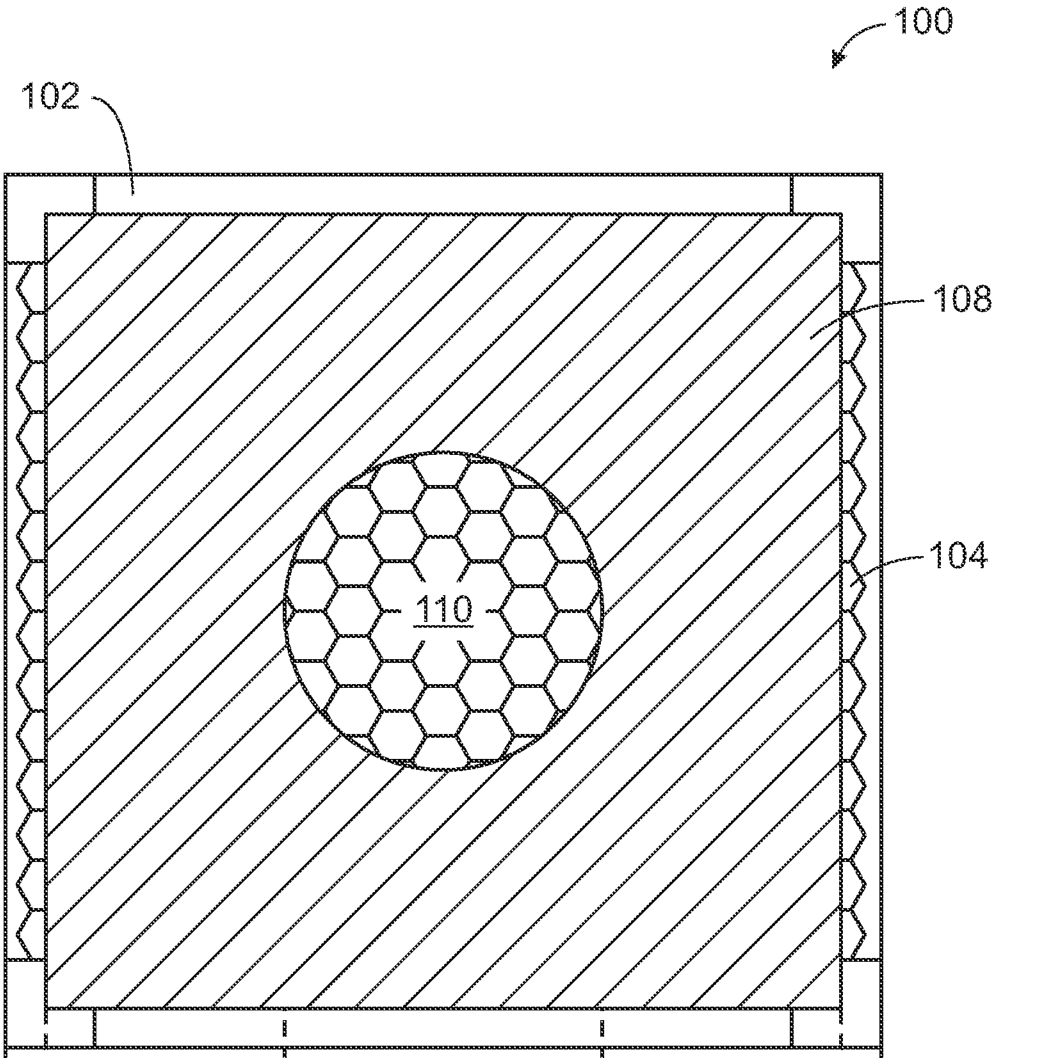
FIG. 1B is a top view of the aromatics detector.
Figure 1C:
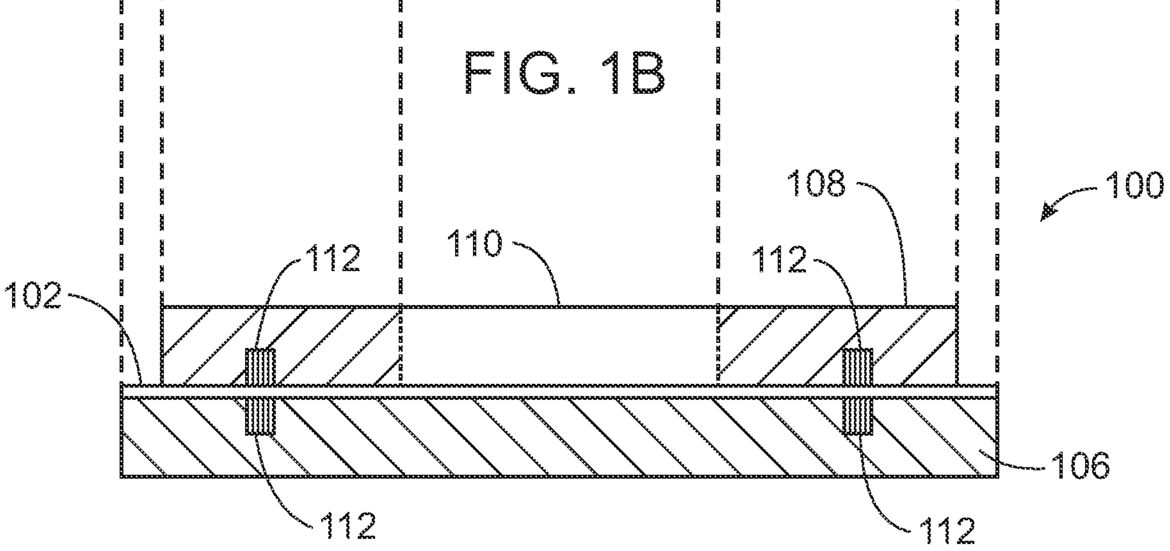
FIG. 1C is a side, cross-sectional view of the aromatics detector.

The device, or aromatics detector, is discussed with respect to FIGS. 1A-1C. The polymer film and resistor mesh are discussed with respect to FIG. 2. The performance of a test is described with respect to FIG. 3. A method for making the polymer film and resistor mesh from a polymer solution is discussed with respect to FIG. 4. The method for using the aromatics detector is discussed with respect to FIG. 5.

FIG. 1A is a perspective view of an aromatics detector 100 based on a polymer film 102 having a resistor mesh 104 deposited over the polymer film 102. In the aromatics detector 100, the polymer film 102 is placed between a lower substrate 106 and an upper substrate 108. An opening 110 in the upper substrate 108 exposes the resistor mesh 104 on the top of the polymer film 102. The opening 110 can be fabricated using a $CO_2$ laser or a mechanical process.

To perform the test, a sample of a fluid is placed on the resistor mesh 104 deposited on the polymer film 102. The sample may be about 0.3 mL, about 0.5 mL, about 1 mL, or about 2 mL, or more. The amount of sample used may depend on the likely concentration of aromatics in the solution.

In various embodiments, the lower substrate 106 comprises polymethyl methacrylate, acetal copolymer, acetal homopolymer, nylon, polytetrafluoroethylene (PTFE), polyvinylidene fluoride copolymer, or glass, or any combinations thereof. In various embodiments, the upper substrate 108 comprises polymethyl methacrylate, acetal copolymer, acetal homopolymer, nylon, polytetrafluoroethylene (PTFE), polyvinylidene fluoride copolymer, or glass, or any combinations thereof. The lower substrate 106 and the upper substrate 108 may be made from different materials.

FIG. 1B is a top view of the aromatics detector 100. The top view shows the opening 110 through which the resistor mesh 104 is accessible. In this view, the resistor mesh 104 is shown in the opening 110. As described herein, during a test, a sample of the test fluid is placed on the resistor mesh 104 through the opening 110.

FIG. 1C is a side, cross-sectional view of the aromatics detector 100. As can be seen in this view, the polymer film 102 is disposed between the lower substrate 106 and the upper substrate 108. In some embodiments, magnets 112 built into the lower substrate 106 and the upper substrate 108 are used to assist with alignment during assembly and hold the lower substrate 106 to the upper substrate 108. In various embodiments, the lower substrate 106 and the upper substrate 108 are held together with mechanical clips, or adhesives, among others.

As materials, such as aromatic compounds, attack the polymer film 102, it will fail, disrupting the resistor mesh 104 and increasing the resistivity. As discussed below, the time to maximum resistivity can be used to indicate the presence of the aromatic compounds from fuels.

Figure 2:
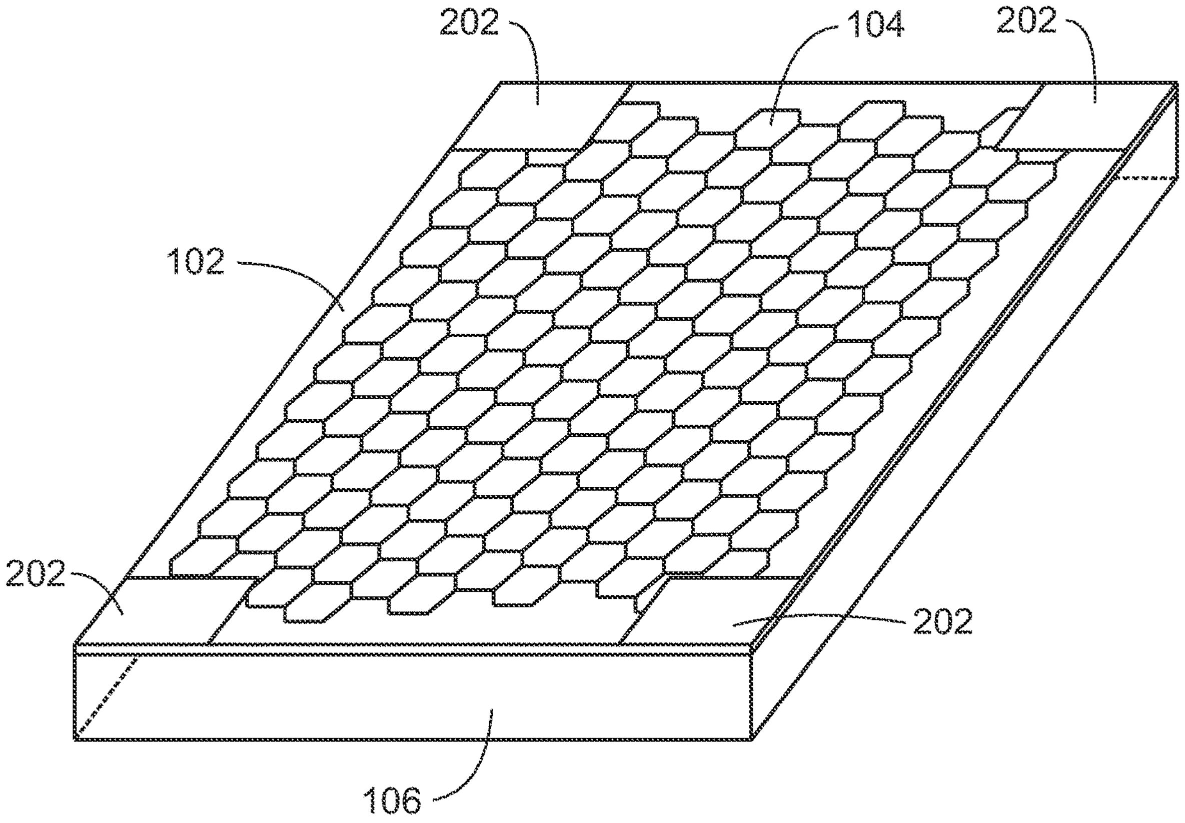
FIG. 2 is a drawing of a polymer film having a resistor mesh disposed over the polymer film.

FIG. 2 is a drawing of a polymer film 102 having a resistor mesh 104 deposited over the polymer film 102. In this illustration, the polymer film 102 is placed on top of the lower substrate 106. In various embodiments, the polymer film 102 is made from a cyclic olefin copolymer (COC), a poly(acrylonitrile butadiene styrene) (ABS), a polyphenylene oxide (PPO), and the like. The choice of the polymer may be used to control the sensitivity of the test, depending on the susceptibility of the polymer to dissolution or stress cracking from components of the sample.

In various embodiments, the resistor mesh 104 is a metal or semiconductor that is deposited through a mask by chemical vapor deposition. The metal can include silver, copper, zinc, or any number of other conductive metals. In some embodiments, the resistor mesh 104 is a semi-conductor, such as indium oxide, gallium arsenide, and the like In various embodiments, the resistor mesh 104 is a conductive substance deposited on the surface of the film by an ink jet printing process. For example, the ink may include carbon particles, metal particles, and the like. Other excipients may be included in the ink, such as polymers, surfactants, or co-solvents, among others. The excipients can be used to stabilize the ink, and improve binding of the resistor mesh 104 to the polymer film 102, among others.

In some embodiments, the resistor mesh 104 has contact pads 202 to enable the measurement of the resistivity changes. The contact pads 202 can be formed with the resistor mesh 104, or may be attached after formation of the resistor mesh 104, for example, by the attachment of metal contacts at the corners using a conductive adhesive. The use of the contact pads is discussed further with respect to FIG. 3.

Figure 3:
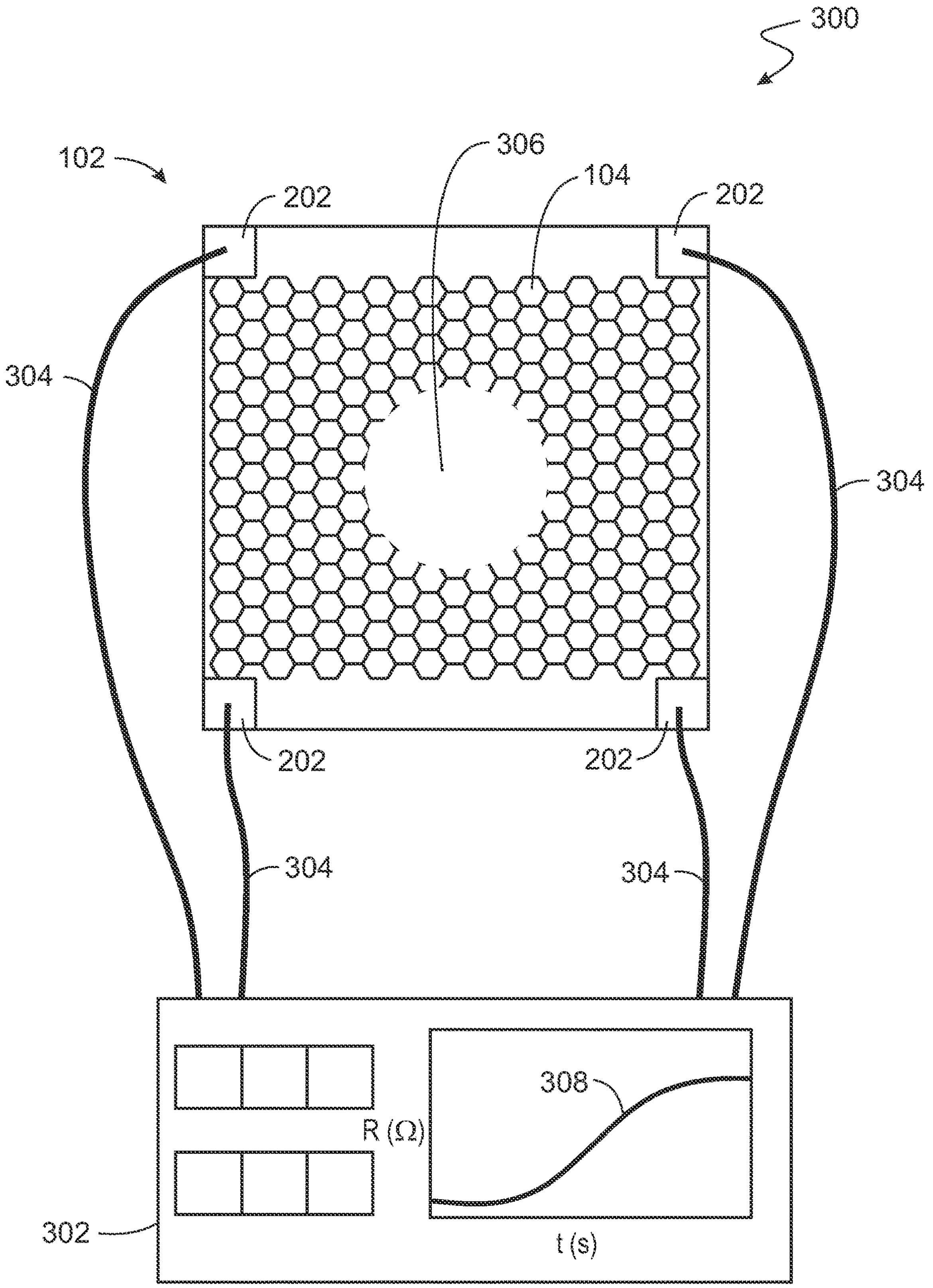
FIG. 3 is a schematic drawing of the resistivity measurement of the resistor mesh during a test.

FIG. 3 is a schematic drawing of the resistivity measurement 300 of the resistor mesh 104 during a test. Like numbered items are as described with respect to previous figures. During the test, a resistivity measurement device 302 is connected to the contact pads 202 by test leads 304. In various embodiments, the resistivity measurement device 302 may include a Wheatstone bridge, a multimeter, an ADC converter coupled to a computer, and the like Although shown as coupled to all four contact pads, the resistivity measurement device 302 may be coupled to a single set of two contact pads 202, for example, placed on the diagonal from each other.

Placing a droplet of a fluid that includes an aromatic solvent on the resistor mesh 104 causes the polymer film 102 under the resistor mesh 104 to dissolve resulting in a disruption 306 of the resistor mesh 104. As the disruption 306 increases in size, the resistivity of the resistor mesh 104 increases, as indicated in this illustration by plot 308. In some embodiments, the resistivity measurement 300 is made by determining the total time between inflection points, for example, by measuring time when the resistivity starts to increase and the time when the resistivity starts to plateau, and comparing the time to that of a control sample that does not have an aromatic component. In some embodiments, the resistivity measurement 300 is made by determining the total increase in resistivity over a certain period of time, and comparing that increase in resistivity to that of a control sample that does not have an aromatic component. Other measurement techniques may also be used.

Figure 4:
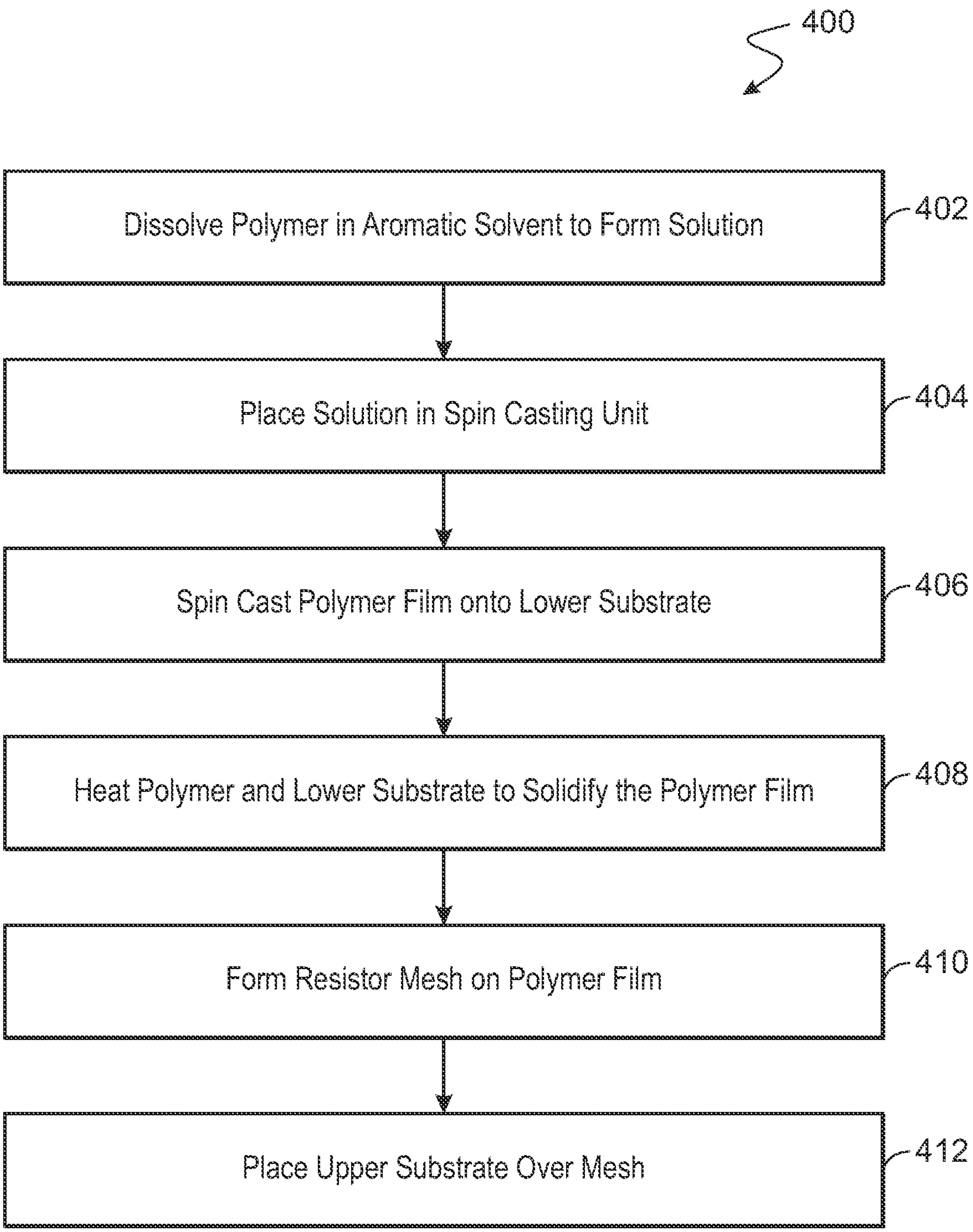
FIG. 4 is a method of making an aromatics detector from a polymer solution.

FIG. 4 is a method 400 of making an aromatics detector from a polymer solution. At block 402, the polymer is dissolved in toluene to form a solution. In various embodiments, the polymer is a cyclic olefin copolymer (COC), an acrylonitrile butadiene styrene copolymer (ABS), or any number of other polymers that are resistant to aliphatic compounds and dissolve or degrade upon exposure to aromatic compounds. At block 404, the solution is placed in a spin-casting unit, for example, being injected through a syringe onto a spinning substrate. At block 406, the polymer film is spin cast as the solution is flowed onto the spinning substrate. The rotating speed and the concentration of the COC, or other polymer, in the solvent controls the thickness of the COC layer. For example, the concentration of the COC in the toluene solvent may range from about 10% to about 30%, or about 20%. The rotational speed of the spin-casting unit can be about 500 to about 5000 rpm, or about 1000 rpm to about 4000 rpm, or about 2000 rpm. The solvent is then evaporated through a baking process that decreases the evaporation time, forming a solid film from the solution. In some embodiments, the substrate used is the lower substrate of the aromatics detector 100 (FIG. 1A-1C). In these embodiments, the upper substrate is set over the resistor mesh 104 of the polymer film 102 during the test.

The concentration of the polymer and the rotation speed in the solvent controls the thickness of the polymer layer. At block 408, the solvent is then evaporated through a baking process that decreases the evaporation time, solidifying a polymer film on the lower substrate.

At block 410, the resistor mesh is formed on the polymer film. As described herein, this may be performed by chemical vapor deposition of a metal or semiconductor on the polymer film, for example, through a mask. Further, the resistor mesh may be made by inkjet printing of an ink containing a conducting material over the polymer film. The conductive material can include carbon black, suspended metal particles, suspended semiconductor particles, or any combination thereof, among others. At block 412, the upper substrate is place over the resistor mesh and secured, for example, by magnets, clips, and the like, as described herein.

In some embodiments, the polymer film is formed by other plastics processing techniques. For example, pellets of the polymer selected are used to form a film, for example, in a sheet extruder or a blown film extruder. The film is then cut into the final size and shape, for example, as shown with respect to FIGS. 1A-1C, and FIG. 2. The resistor mesh can then be formed over the polymer film, as described with respect to block 410. This technique may be advantageous as the aromatics detector may be disassembled after testing, cleaned, a fresh film they are inserted, then reused.

Figure 5:
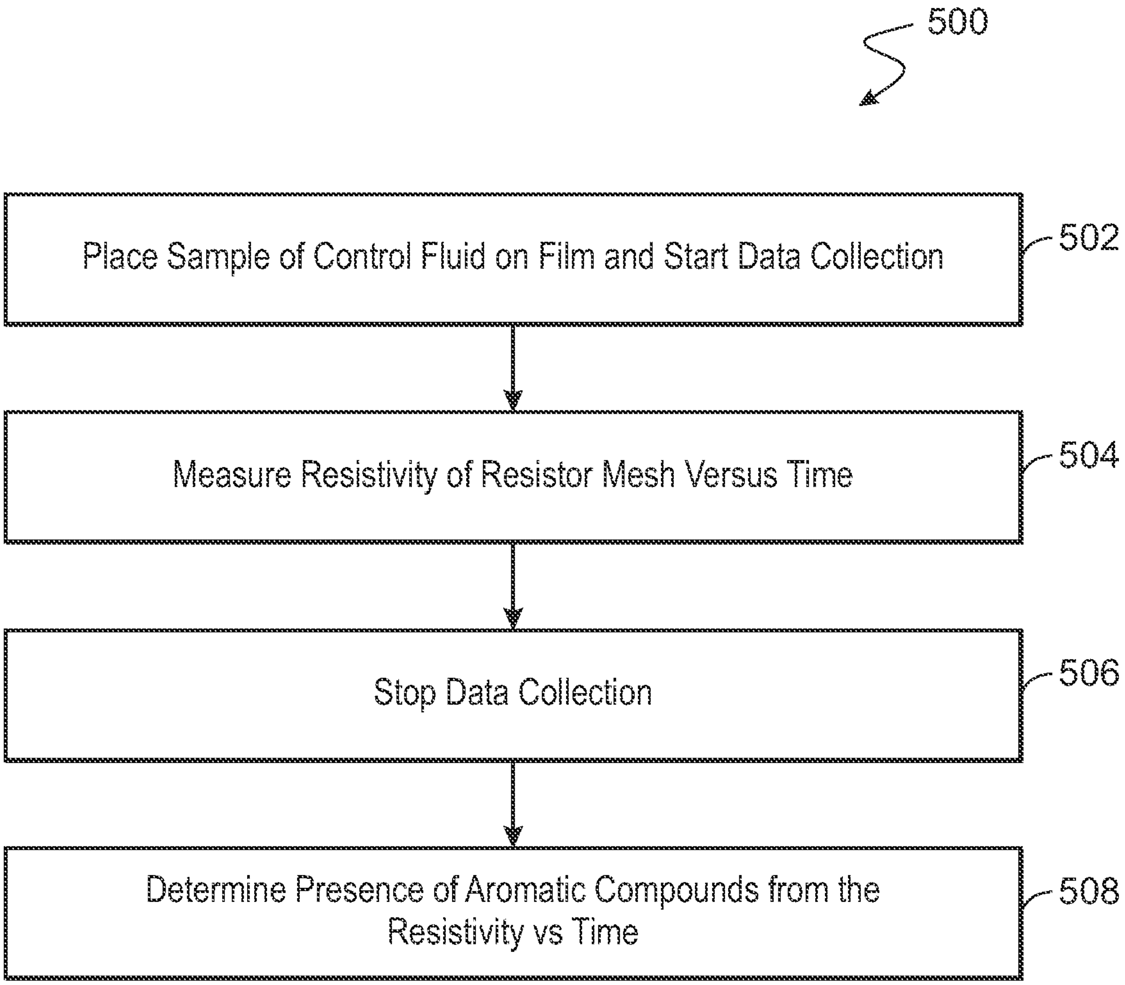
FIG. 5 is a method of using an aromatics detector to determine the presence of aromatics mixed into a matrix of aliphatic compounds.

FIG. 5 is a method 500 of using an aromatics detector to determine the presence of aromatics mixed into a matrix of aliphatic compounds. The method begins at block 502 when a sample of a control fluid is placed on the resistor mesh over the polymer film, for example, and data collection is started. At block 504, the resistivity of the resistor mesh is measured over time. At block 506, the data collection is stopped, for example, wherein the resistivity has plateaued or after a predetermined time.

At block 508, the time for the resistivity to plateau, for example, the time between a first inflection point and a second inflection point in a resistivity versus time graph, is used to determine the presence of an aromatic contaminant in an aliphatic solvent. This may be performed by comparing the time to a control sample.

The test procedure is not limited to the specific steps shown in the blocks above. For example, if the polymer used to form the polymer film is not susceptible to dissolution by aliphatic compounds, the test may be implemented with no control fluid. In this example, a few milliliters of the test sample is placed on the polymer film through the opening of the upper substrate, and the change in resistivity indicates the presence of the aromatic compounds.

Examples

The design tested for the diesel-sensitive element of the sensor included a thin film of cyclic olefin copolymer (COC) with a conductive line, of silver or gold, sputtered on top. The COC film had a thickness of around 10-15 μm, where the thickness is inversely proportional to the dissolution rate, thus having a thin film helps achieve faster results.

Forming the COC Film

The formation of a COC film was tested. The COC was purchased from TOPAS advanced polymers of Florence, KY, USA. The great selected was 5013I-10 which had 3 mm nominal granule size.

A COC solution was first made using 30% (w/w) of COC crystals dissolved in Toluene. The solution was then spin coated at a speed of 1500 rpm for 30 sec and then heated on a hot plate of 40° C. to dry the COC thin film. The film was then released from the carrier wafer.

Forming the Conductive Line

A polyimide mask of the conductive line was designed. The mask was taped on the stage directly by covering over the COC film covered wafer without direct contact with the COC film. It was then sputtered using a silver target. In the tests herein, the conductive trace was used as a fuse for a circuit driving a light-emitting diode.

Design with Glass Substrate

Initially, the COC film was affixed to a glass substrate for support. Acrylic frame was cut to attach on top of the glass-COC-gold stack, to act as holder for the drop casted diesel.

Design with Released COC Thin Film

To achieve this, the COC thin film was released from the substrate using acetone. The film was subsequently sputtered and diced to make samples for testing. The film was placed between two acrylic frames.

Embodiments

An embodiment described herein provides a system for detecting aromatic compounds mixed with aliphatic compounds. The system includes a lower substrate, a polymer film including a resistor mesh disposed on the polymer film, and an upper substrate disposed over the polymer film, wherein the upper substrate includes an opening exposing the resistor mesh.

In an aspect, the lower substrate includes glass. In an aspect, the lower substrate includes acetal copolymer, acetal homopolymer, nylon, polytetrafluoroethylene (PTFE), or polyvinylidene fluoride, or any combination thereof.

In an aspect, the polymer film includes a cyclic olefin copolymer (COC). In an aspect, the polymer film includes poly(acrylonitrile butadiene styrene) (ABS). In an aspect, the polymer film includes polyphenylene oxide (PPO).

In an aspect, the resistor mesh includes metal particles printed on the polymer film. In an aspect, the resistor mesh includes a metal trace deposited on the polymer film. In an aspect, the metal trace is deposited on the polymer film by chemical vapor deposition through a mask.

In an aspect, the upper substrate includes glass. In an aspect, the upper substrate includes acetal copolymer, acetal homopolymer, nylon, polytetrafluoroethylene (PTFE), or polyvinylidene fluoride, or any combination thereof.

Another embodiment described herein provides a method for detecting aromatic compounds mixed with aliphatic compounds. The method includes placing a sample of a test fluid on a polymer film through an opening in an upper substrate, wherein a resistor mesh is disposed on the polymer film. Data collection is started when the sample contacts the resistor mesh, wherein the data collection measures resistivity over time. The data collection is stopped, and a change in resistivity over time is used to determine a test time. The test time is used to determine if an aromatic compound is present in the test fluid.

In an aspect, the method includes determining a test time based, at least in part, on the time at which the resistivity starts to plateau, as determined by a difference in time between a first inflection point in the resistivity and a second inflection point in the resistivity.

In an aspect, the method includes assembling a test apparatus with a layer of polymer film, between two substrates, wherein an upper substrate has an opening to the resistor mesh disposed on the polymer film. In an aspect, the method includes removing the polymer film from the test apparatus after a test is completed, cleaning the test apparatus, and reassembling the test apparatus with a replacement layer of the polymer film between the upper substrate and a lower substrate, wherein the resistor mesh on the layer polymer film faces the opening in the upper substrate.

In an aspect, the method includes placing a sample of control fluid on the resistor mesh disposed on the polymer film through the opening in the upper substrate, starting data collection when the sample contacts the resistor mesh, wherein the data collection measures resistivity over time, and stopping the data collection. A change in resistivity over time is used to determine a control time. In an aspect, the method includes comparing the test time to the control time to determine if an aromatic compound is present at a test fluid.

In an aspect, the method includes forming the polymer film by dissolving a polymer in an aromatic solvent to form a solution, and casting the polymer film. In an aspect, the polymer includes a cyclic olefin copolymer.

In an aspect, the method includes forming the resistor mesh by printing a conductive ink on the polymer film. In an aspect, the method includes forming the resistor mesh by chemical vapor deposition of a conductive material through a mask on the polymer film.

In an aspect, the polymer includes an acrylonitrile butadiene styrene (ABS) copolymer.

Other implementations are also within the scope of the following claims.

What is claimed is:

1. A system for detecting aromatic compounds mixed with aliphatic compounds, comprising:

a lower substrate;

a polymer film comprising a resistor mesh disposed on the polymer film; and an upper substrate disposed over the polymer film, wherein the upper substrate comprises an opening exposing the resistor mesh;

contact pads coupled to the to the resistor mesh; and a resistivity measurement device having test leads coupled to the contact pads, wherein the resistivity measurement device is configured to measure a change in resistivity of the resistor mesh.

2. The system of claim 1, wherein the lower substrate comprises glass.

3. The system of claim 1, wherein the lower substrate comprises acetal copolymer, acetal homopolymer, nylon, polytetrafluoroethylene (PTFE), or polyvinylidene fluoride, or any combination thereof.

4. The system of claim 1, wherein the polymer film comprises a cyclic olefin copolymer (COC).

5. The system of claim 1, wherein the polymer film comprises poly(acrylonitrile butadiene styrene) (ABS).

6. The system of claim 1, wherein the polymer film comprises polyphenylene oxide (PPO).

7. The system of claim 1, wherein the resistor mesh comprises metal particles printed on the polymer film.

8. The system of claim 1, wherein the resistor mesh comprises metal traces deposited on the polymer film.

9. The system of claim 8, wherein the metal traces are deposited on the polymer film by chemical vapor deposition through a mask.

10. The system of claim 1, wherein the upper substrate comprises glass.

11. The system of claim 1, wherein the upper substrate comprises acetal copolymer, acetal homopolymer, nylon, polytetrafluoroethylene (PTFE), or polyvinylidene fluoride, or any combination thereof.

* * * * *